(12) United States Patent
Crouch et al.

(10) Patent No.: US 11,951,222 B2
(45) Date of Patent: Apr. 9, 2024

(54) ULTRA-COMPACT PORTABLE SOLAR-POWERED THERMO-CHEMICAL DECONTAMINATION SYSTEM AND METHOD

(71) Applicant: Raytheon Company, Waltham, MA (US)

(72) Inventors: David D. Crouch, Riverside, CA (US); Alf L. Carroll, III, Marion, MA (US); John Carcone, Portsmouth, RI (US); Travis B. Feenstra, Calimesa, CA (US); David R. Sar, Marana, AZ (US); Anthony Serino, Northborough, MA (US)

(73) Assignee: Raytheon Company, Tewksbury, MA (US)

( * ) Notice: Subject to any disclaimer, the term of this patent is extended or adjusted under 35 U.S.C. 154(b) by 697 days.

(21) Appl. No.: 17/124,208

(22) Filed: Dec. 16, 2020

(65) Prior Publication Data

US 2022/0184256 A1    Jun. 16, 2022

(51) Int. Cl.
*A61L 2/18*    (2006.01)
*A61L 2/08*    (2006.01)
(Continued)

(52) U.S. Cl.
CPC .............. *A61L 2/186* (2013.01); *A61L 2/084* (2013.01); *F24S 23/74* (2018.05); *F24S 50/80* (2018.05);
(Continued)

(58) Field of Classification Search
CPC ............ A61L 2/186; F24S 50/80; F24S 23/74
(Continued)

(56) References Cited

U.S. PATENT DOCUMENTS

| 4,083,357 A | * | 4/1978 | Fischer | F24S 20/30 |
| | | | | 126/696 |
| 4,205,661 A | * | 6/1980 | Chapman | F24S 23/30 |
| | | | | 126/606 |

(Continued)

FOREIGN PATENT DOCUMENTS

| CN | 109959175 A | 7/2019 |
| IT | UB20155600 A1 | 5/2017 |
| WO | 2017223224 A1 | 12/2017 |

OTHER PUBLICATIONS

International Search Report and Written Opinion of the International Searching Authority dated Apr. 7, 2022 in connection with International Patent Application No. PCT/US2021/061192, 12 pages.

(Continued)

*Primary Examiner* — Vivek K Shirsat

(57) ABSTRACT

A system includes a containment vessel configured to receive and retain equipment to be decontaminated. The system also includes a solar reflector configured to reflect solar energy towards the containment vessel in order to heat the containment vessel. The system further includes end supports configured to receive and retain the solar reflector and the containment vessel. The system also includes a base having or coupled to multiple side supports, where each side support is configured to contact and support a corresponding one of the end supports. In addition, the system includes one or more semi-transparent solar shades configured to reduce the solar energy reaching the solar reflector and the containment vessel.

20 Claims, 8 Drawing Sheets

(51) Int. Cl.
*F24S 23/74* (2018.01)
*F24S 25/00* (2018.01)
*F24S 25/60* (2018.01)
*F24S 50/80* (2018.01)

(52) U.S. Cl.
CPC ..... *A61L 2202/122* (2013.01); *A61L 2202/14* (2013.01); *F24S 2025/01* (2018.05); *F24S 2025/6007* (2018.05)

(58) Field of Classification Search
USPC .................................. 126/569–713, 692–695
See application file for complete search history.

(56) References Cited

U.S. PATENT DOCUMENTS

| | | | |
|---|---|---|---|
| 4,262,660 A | 4/1981 | Ilich | |
| 4,587,452 A | 5/1986 | Okumura et al. | |
| 4,766,941 A * | 8/1988 | Sloop | E06B 9/72 160/310 |
| 8,844,135 B2 * | 9/2014 | Denkmann | F24S 23/82 29/458 |
| 9,222,665 B2 | 12/2015 | Halas et al. | |
| 9,878,061 B2 | 1/2018 | Shur et al. | |
| 10,654,726 B2 | 5/2020 | Nigrelli | |
| 2011/0023868 A1 | 2/2011 | Seller | |
| 2016/0003496 A1 * | 1/2016 | Brenmiller | F24S 23/74 126/606 |
| 2016/0305691 A1 | 10/2016 | Sherwin | |
| 2016/0352022 A1 | 12/2016 | Thomson et al. | |
| 2017/0021047 A1 | 1/2017 | Gazzelli et al. | |

OTHER PUBLICATIONS

Carlson et al. "Solar powered water purification system," Mechanical Engineering Senior Theses, Santa Clara University, Jan. 2012, 160 pages.
Chandler, "Sterilizing with the sun: Solar concentrating system could replace fuel-powered or electric devices in remote villages," Phys.org News, Feb. 2013, 3 pages.
"Sterilizing medical tools off the grid using solar heat," Innovation Toronto, Dec. 2020, 5 pages.
"Preppers Peak Solar Cooker Kettle for Camping Outdoor Travel with Solar Technology," Kettles for Water, Dec. 2020, 2 pages.
Lu, "Portable device uses solar power to sterilise medical equipment," NewScientist, Nov. 2020, 6 pages.
"Parabolic Solar Trough—Thermal Water Heater," Parabolic Trough Concentrated Solar Power, Dec. 2020, 6 pages.
Roel, "350mm f/4 lightweight truss Dobson (airline transportable)," DIY Astronomer, Stargazers Lounge, Dec. 2013, 23 pages.
Sherwin, "GoSun Sport: Portable, High Efficiency Solar Cooker," Kickstarter, May 2019, 29 pages.
"Food Cooking Medical Sterilization and Ice Making (adsorption process) with the Soleil-Vapeur Solar Thermal Steam Unit," soleil-vapeur.org, Oct. 2014, 4 pages.
Carroll et al., "Low-Cost Rapid Thermo-Chemical Decontamination Process for Facemasks or Other Personal Protection Equipment (PPE) and Related System and Apparatus," U.S. Appl. No. 17/169,260, filed Feb. 5, 2021, 39 pages.
Crouch et al., "Solar-Heater Thermo-Chemical Decontamination System for Facemasks or Other Personal Protection Equipment (PPE)," U.S. Appl. No. 16/986,761, filed Aug. 6, 2020, 32 pages.
Crouch et al., "Containment Vessels for Rapid Thermo-Chemical Decontamination of Facemasks or Other Personal Protection Equipment (PPE)," U.S. Appl. No. 16/944,617, filed Jul. 31, 2020, 43 pages.

* cited by examiner

US 11,951,222 B2

ULTRA-COMPACT PORTABLE SOLAR-POWERED THERMO-CHEMICAL DECONTAMINATION SYSTEM AND METHOD

TECHNICAL FIELD

This disclosure relates generally to medical decontamination systems and processes. More specifically, this disclosure relates to an ultra-compact portable solar-powered thermo-chemical decontamination system and method.

BACKGROUND

A dangerous gap has developed in the available supply of disposable facemasks, such as N95/KN95/N99/N100/P100 surgical masks, and other personal protection equipment (PPE), such as surgical gowns, booties, and gloves, as a result of the COVID-19 pandemic. Accelerating demand has outstripped the ability of the supply chain to keep pace. As a result, medical staff are (among other things) routinely forced to use a large amount of personal protection equipment and, in some cases, wear the same masks or other personal protection equipment to treat multiple patients, which poses a cross-contamination hazard to patients and medical personnel. An additional risk is mask "breakthrough" in which contaminants eventually diffuse through a mask and infect the wearer.

SUMMARY

This disclosure provides an ultra-compact portable solar-powered thermo-chemical decontamination system and method.

In a first embodiment, an apparatus includes a solar reflector configured to reflect solar energy towards a containment vessel. The apparatus also includes end supports configured to receive and retain the solar reflector and the containment vessel. The apparatus further includes a base having or coupled to multiple side supports, where each side support is configured to contact and support a corresponding one of the end supports. In addition, the apparatus includes one or more semi-transparent solar shades configured to reduce the solar energy reaching the solar reflector and the containment vessel.

In a second embodiment, a system includes a containment vessel configured to receive and retain equipment to be decontaminated. The system also includes a solar reflector configured to reflect solar energy towards the containment vessel in order to heat the containment vessel. The system further includes end supports configured to receive and retain the solar reflector and the containment vessel. The system also includes a base having or coupled to multiple side supports, where each side support is configured to contact and support a corresponding one of the end supports. In addition, the system includes one or more semi-transparent solar shades configured to reduce the solar energy reaching the solar reflector and the containment vessel.

In a third embodiment, a method includes inserting a containment vessel containing equipment to be decontaminated between end supports of a decontamination system. The method also includes reflecting solar energy towards the containment vessel using a solar reflector of the decontamination system, where edges of the solar reflector are received and retained by the end supports. The method further includes, using a base having or coupled to multiple side supports, supporting the end supports and allowing the end supports to rotate in order to aim the solar reflector. In addition, the method includes using one or more semi-transparent solar shades to control the solar energy reaching the solar reflector.

Other technical features may be readily apparent to one skilled in the art from the following figures, descriptions, and claims.

BRIEF DESCRIPTION OF THE DRAWINGS

For a more complete understanding of this disclosure, reference is made to the following description, taken in conjunction with the accompanying drawings, in which.

DETAILED DESCRIPTION

Figure 1:
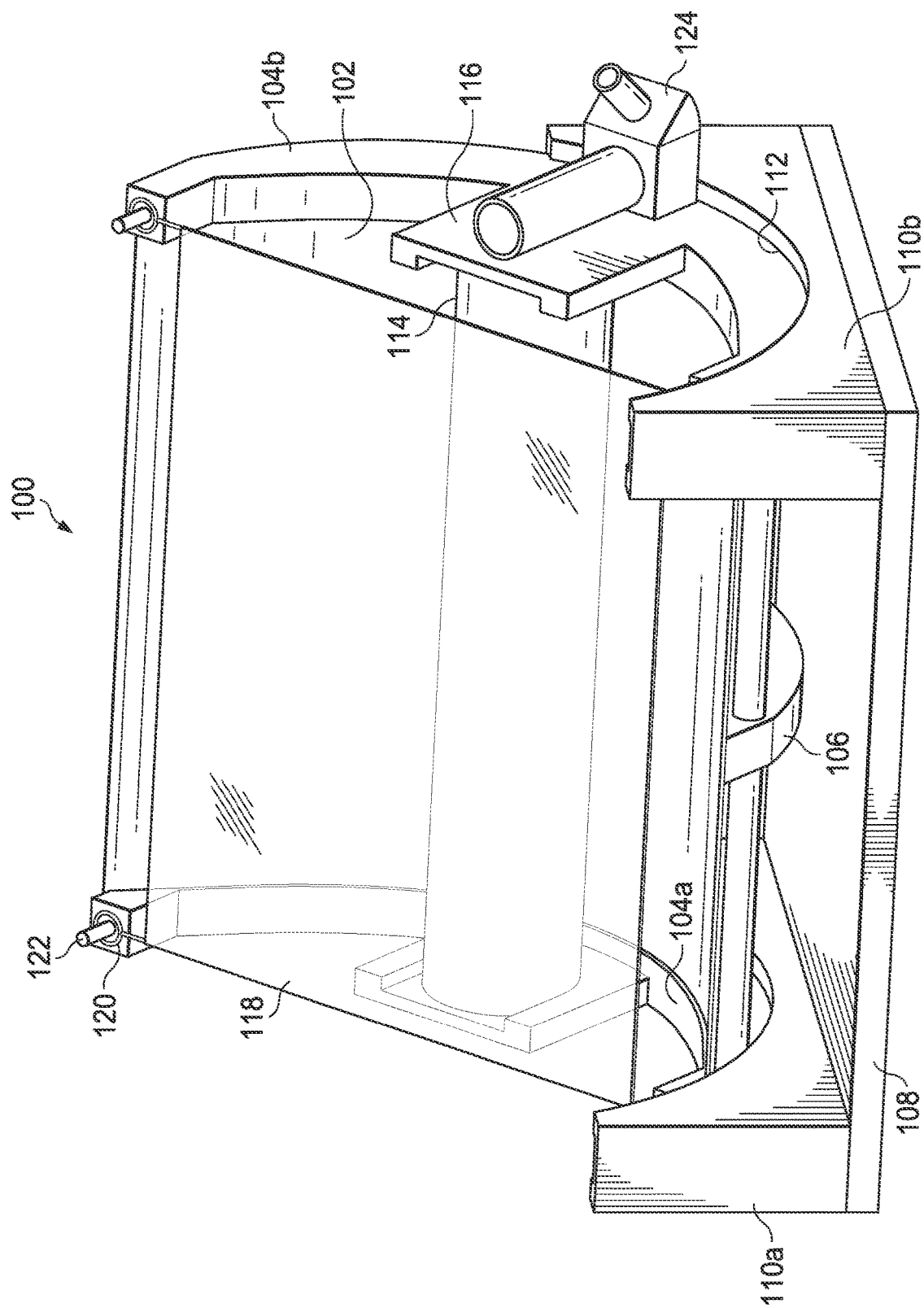
FIG. 1 illustrates an example ultra-compact portable solar-powered thermo-chemical decontamination system in accordance with this disclosure.

FIGS. 1 through 9, described below, and the various embodiments used to describe the principles of the present disclosure are by way of illustration only and should not be construed in any way to limit the scope of the disclosure. Those skilled in the art will understand that the principles of the present disclosure may be implemented in any type of suitably arranged device or system.

As noted above, a dangerous gap has developed in the available supply of disposable facemasks, such as N95/KN95/N99/N100/P100 surgical masks, and other personal protection equipment (PPE), such as surgical gowns, booties, and gloves, as a result of the COVID-19 pandemic. Disposable facemasks are sometimes referred to as surgical respirators. Accelerating demand has outstripped the ability of the supply chain to keep pace. As a result, medical staff are (among other things) routinely forced to use a large amount of personal protection equipment and, in some cases, wear the same masks or other personal protection equipment to treat multiple patients. This poses a cross-contamination hazard to patients and medical personnel and poses an additional risk related to mask "breakthrough" in which contaminants eventually diffuse through a mask and infect the wearer. Under normal circumstances, facemasks, surgical gowns, booties, gloves, and other personal protection equipment may typically be disposable, meaning they are worn once and discarded. However, when supplies run low (such as during a pandemic), it may be necessary or desirable to decontaminate and reuse facemasks, surgical gowns, booties, gloves, and other personal protection equipment.

Some approaches for decontaminating personal protection equipment involve the use of hydrogen peroxide ($H_2O_2$)

vapor to decontaminate the equipment. However, these approaches may take an extended period of time (such as about 8 hours) to complete, which can be problematic in environments where a large amount of personal protection equipment is used. These approaches may also require high concentrations of hydrogen peroxide (such as 35% compared to about 3% to 6% over-the-counter solutions), which can be toxic and potentially explosive. Other approaches for decontaminating personal protection equipment involve the use of ultraviolet germicidal irradiation in which the equipment is illuminated using ultraviolet light, which can deactivate or kill bacteria and viruses. However, inner layers of a facemask or other personal protection equipment may not receive a high enough dose of ultraviolet radiation, and light transmittance varies among equipment. Also, straps or other structures of personal protection equipment can present a residual contamination risk and may require a secondary decontamination process, and it is often challenging to ensure that all surfaces/layers of personal protection equipment are completely decontaminated due to shadowing effects. Still other approaches for decontaminating personal protection equipment involve the use of microwave-generated or solar-generated steam, which is an effective technique for decontaminating medical instruments and other materials used every day in surgeries, procedures, and patient services. However, when used with disposable personal protection equipment, microwave-generated or solar-generated steam runs the risk of overheating the equipment, causing damage or degradation. If a facemask is even slightly deformed by heating to excessive temperatures, it can lose its ability to protect the wearer and must be discarded.

This disclosure provides an ultra-compact portable solar-powered thermo-chemical decontamination system. As described in more detail below, the decontamination system can be used to support a decontamination process, such as one that uses heating in combination with a low-concentration hydrogen peroxide solution, to rapidly decontaminate personal protection equipment or other equipment in order to facilitate safe reuse of the equipment, such as during pandemic-induced shortages. The decontamination system uses a solar reflector (such as a parabolic cylindrical reflector) to focus incident solar energy onto a containment vessel (such as a cylindrical containment vessel). The solar energy heats the personal protection equipment or other equipment and the low-concentration hydrogen peroxide solution within the containment vessel in order to decontaminate the equipment in the containment vessel. The decontamination system is adjustable in order to help point the solar reflector in a desired direction, such as by adjusting the elevation and azimuth of the solar reflector to point directly at the sun. The system may also include one or more solar shades to help control the amount of solar energy being directed towards the containment vessel.

Low-concentration hydrogen peroxide solutions (such as about 3% to 6%) are routinely available in a medical setting (such as a standard hospital or a mobile Army surgical hospital (MASH) setting) or in a commercial setting (such as a pharmacy or grocery store). Thus, various components and chemicals used to support the decontamination process are typically already available in a setting and can be used here. Moreover, as described below, peak temperatures experienced by the personal protection equipment or other equipment during the decontamination process can be limited to a suitable range, such as about 65° C. to about 80° C., which prevents damage to the equipment or degradation of the equipment's fit or function while being adequate to deactivate or kill pathogens or otherwise decontaminate the equipment.

In this way, synergy is achieved by attacking contaminants with both moist heating and hydrogen peroxide, yielding faster and more effective decontamination than either approach used alone. Also, the lower-temperature decontamination process protects facemasks or other personal protection equipment from damage or degradation, and the use of materials such as about 3% to about 6% hydrogen peroxide solution avoids toxic concentrations and potential explosiveness of higher concentrations. Moreover, some embodiments can reduce or minimize the weight of the decontamination system, and the decontamination system may be easily assembled, disassembled, and stowed in a compact volume (such as a backpack) for storage or transport. Among other things, this can be accomplished by implementing the solar reflector using one or more normally-flat flexible reflectors that are held to shape by support structures of the decontamination system. When the decontamination system is disassembled, the one or more pieces of the solar reflector can revert back to a flattened shape. This may allow for transport and use of the decontamination system in various applications, such as when used in locations where electricity distribution is unreliable, locations that have experienced natural disasters, or back-country locations. In addition, the amount of solar energy being collected by the decontamination system can be controlled using the solar shade(s) to help provide improved temperature control during the decontamination process.

FIG. 1 illustrates an example ultra-compact portable solar-powered thermo-chemical decontamination system 100 in accordance with this disclosure. As shown in FIG. 1, the decontamination system 100 includes a solar reflector 102, which is configured to receive and reflect solar energy in a concentrated fashion. The solar reflector 102 may be formed from any suitable material(s), such as one or more metals or other highly-reflective materials, and in any suitable manner. As a particular example, the solar reflector 102 may be formed using a light-weight highly-reflective foil or a sheet of metalized plastic. In some embodiments, the solar reflector 102 is foldable or flexible so that the solar reflector 102 can be manipulated into desired shapes during assembly, disassembly, and stowage. For instance, the solar reflector 102 may be flat or rolled while stowed and curved while in use. The solar reflector 102 may be fabricated as a single structure or as multiple structures that can be assembled to form the solar reflector 102. The use of multiple structures to form the solar reflector 102 may help to allow stowage of the solar reflector 102 in a smaller amount of space compared to the use of a single larger structure, although nothing prevents a single structure from being used here for the solar reflector 102.

The solar reflector 102 is held in place using two end supports 104a-104b and at least one optional additional support 106. Each end support 104a-104b may engage with or otherwise contact the solar reflector 102 in order to help hold the solar reflector 102 in place. If the solar reflector 102 is foldable or flexible, the end supports 104a-104b can also help to hold the solar reflector 102 in a desired shape. Each additional support 106 may be positioned between the end supports 104a-104b in order to provide additional structural support to the solar reflector 102. Each end support 104a-104b and each additional support 106 may be formed from any suitable material(s), such as light-weight rugged plastic. Each end support 104a-104b and each additional support 106 may also be formed in any suitable manner, such as additive manufacturing, injection molding, casting, machining, or other suitable technique.

A base 108 of the decontamination system 100 represents a lower portion of the decontamination system 100. The base 108 can be placed on the ground, on a table, or in any other desired location that has exposure to the sun. The base 108 includes or is coupled to two side supports 110a-110b, which can contact the end supports 104a-104b and hold the end supports 104a-104b in place. Each side support 110a-110b can include a groove 112 that is configured to receive the lower edge of one of the end supports 104a-104b. The grooves 112 allow the end supports 104a-104b to be rotated in order to aim the solar reflector 102 while friction holds the end supports 104a-104b in place otherwise, thereby providing a mount for the solar reflector 102 similar to that used with Dobsonian telescopes. The base 108 and each side support 110a-110b may be formed from any suitable material(s), such as light-weight rugged plastic. The base 108 and each side support 110a-110b may also be formed in any suitable manner, such as additive manufacturing, injection molding, casting, machining, or other suitable technique.

A containment vessel 114 is configured to be held in place within the decontamination system 100 between the end supports 104a-104b and be heated using solar energy reflected from the solar reflector 102. The containment vessel 114 here generally takes the form of a cylindrical vessel into which any suitable amount of personal protection equipment or other equipment can be placed. The containment vessel 114 can also receive a low-concentration hydrogen peroxide solution that is at least partially vaporized during a decontamination process to help decontaminate the personal protection equipment or other equipment in the containment vessel 114. In some embodiments, the containment vessel 114 may include an elongated cylindrical body, as well as a lid that can be attached and sealed to or unsealed and removed from the cylindrical body. The use of a seal helps to retain water, hydrogen peroxide, contaminants, or other materials inside the containment vessel 114 until a decontamination process is completed. The containment vessel 114 may be formed from any suitable material(s), such as one or more metals or light-weight rugged plastic. The containment vessel 114 may also be formed in any suitable manner, such as additive manufacturing, injection molding, casting, machining, or other suitable technique.

In some embodiments, the containment vessel 114 may optionally include at least one pressure-relief valve. The pressure-relief valve includes any suitable structure configured to be selectively opened and closed to provide or block a pathway for pressure to escape from an interior volume of the containment vessel 114. The pressure-relief valve allows the interior volume of the containment vessel 114 to be sealed during heating of the equipment, thereby increasing the pressure within the containment vessel 114 during the heating. Among other things, this helps to keep hydrogen peroxide vapor surrounding the equipment during a decontamination process. Once the decontamination process is completed, the pressure-relief valve can be opened in order to allow excess pressure in the containment vessel 114 to be relieved. At that point, the equipment can be removed from the containment vessel 114 for drying, or the containment vessel 114 can be reheated (with the pressure-relief valve opened) to dry the equipment.

In some cases, the pressure-relief valve may include an integrated filter or otherwise be used in conjunction with a filter. The filter may be used to filter air or other fluid passing out of the containment vessel 114, such as during or after heating of the containment vessel 114. For instance, after being heated for a specified period of time, the pressure-relief valve may be opened, and the filter may filter air passing out of the containment vessel 114. Among other things, this may help to prevent contamination of air or nearby surfaces during use of the containment vessel 114. Each filter includes any suitable structure configured to remove contaminants or other materials from fluid, such as a HEPA filter.

In this example, the containment vessel 114 is held in place using two projections 116 of the end supports 104a-104b. For example, the containment vessel 114 may slide into and along the projections 116 until the containment vessel 114 reaches a desired location as defined by the projections 116. In some cases, the containment vessel 114 is positioned such that, during a decontamination process, the central longitudinal axis of the containment vessel 114 substantially coincides with the focal line of the solar reflector 102, which helps to maximize irradiance and heating of the containment vessel 114. Of course, the containment vessel 114 may have any other suitable position within the decontamination system 100.

At least one solar shade 118 may optionally be positioned in front of the solar reflector 102 and the containment vessel 114 in order to control heating of the containment vessel 114. For example, each solar shade 118 may be semi-transparent in order to reduce the solar flux reaching the solar reflector 102. Depending on the implementation, there may be a single solar shade 118 or multiple solar shades 118 provided for use. If multiple solar shades 118 are provided, the solar shades 118 may be used individually or collectively (such as in a stacked manner) to provide a desired amount of solar flux control. As a particular example, multiple solar shades 118 each having a common semi-transparency may be provided, and (if a single solar shade 118 is inadequate to provide a desired amount of solar flux control) multiple solar shades 118 may be stacked to provide the desired amount of solar flux control. Note, however, that it may also or alternatively be possible to use solar shades 118 with different amounts of semi-transparencies. Each solar shade 118 may be formed using any suitable material(s), such as one or more partially transparent materials, and in any suitable manner.

In this example, each solar shade 118 is removably mounted to the end supports 104a-104b using connectors 120, which can be placed over projections 122 extending from the end supports 104a-104b. In this example, each connector 120 represents a ring that can be placed over an associated projection 122, where each ring is attached to the solar shade 118 by an elastic band or other link. However, any other suitable connectors 120 may be used here to allow one or more solar shades 118 to be removably mounted to the decontamination system 100. For instance, the multiple connectors 120 may take the form of holes formed in each solar shade 118. Each projection 122 may have any suitable form that can be used with a connector 120 of at least one solar shade 118. Note, however, that the use of connectors 120 and projections 122 is optional and that one or more solar shades 118 may be mounted on or otherwise attached to the decontamination system 100 in any other suitable manner.

A telescope 124 is mounted on or otherwise attached to the decontamination system 100. In this example, the telescope 124 is mounted to the end support 104b, although the telescope 124 may have any other suitable position. The telescope 124 may be used to aim the solar reflector 102 in a desired direction, such as directly at the sun. The telescope 124 includes any suitable structure configured to aim the solar reflector 102. In this example, the telescope 124 represents a Newtonian reflector telescope, although the telescope 124 may have any other suitable form (and may or may not provide telescopic operation or optical magnification). The telescope 124 can include one or more internal solar filters to prevent eye damage to a user and crosshairs for alignment.

Figure 2:
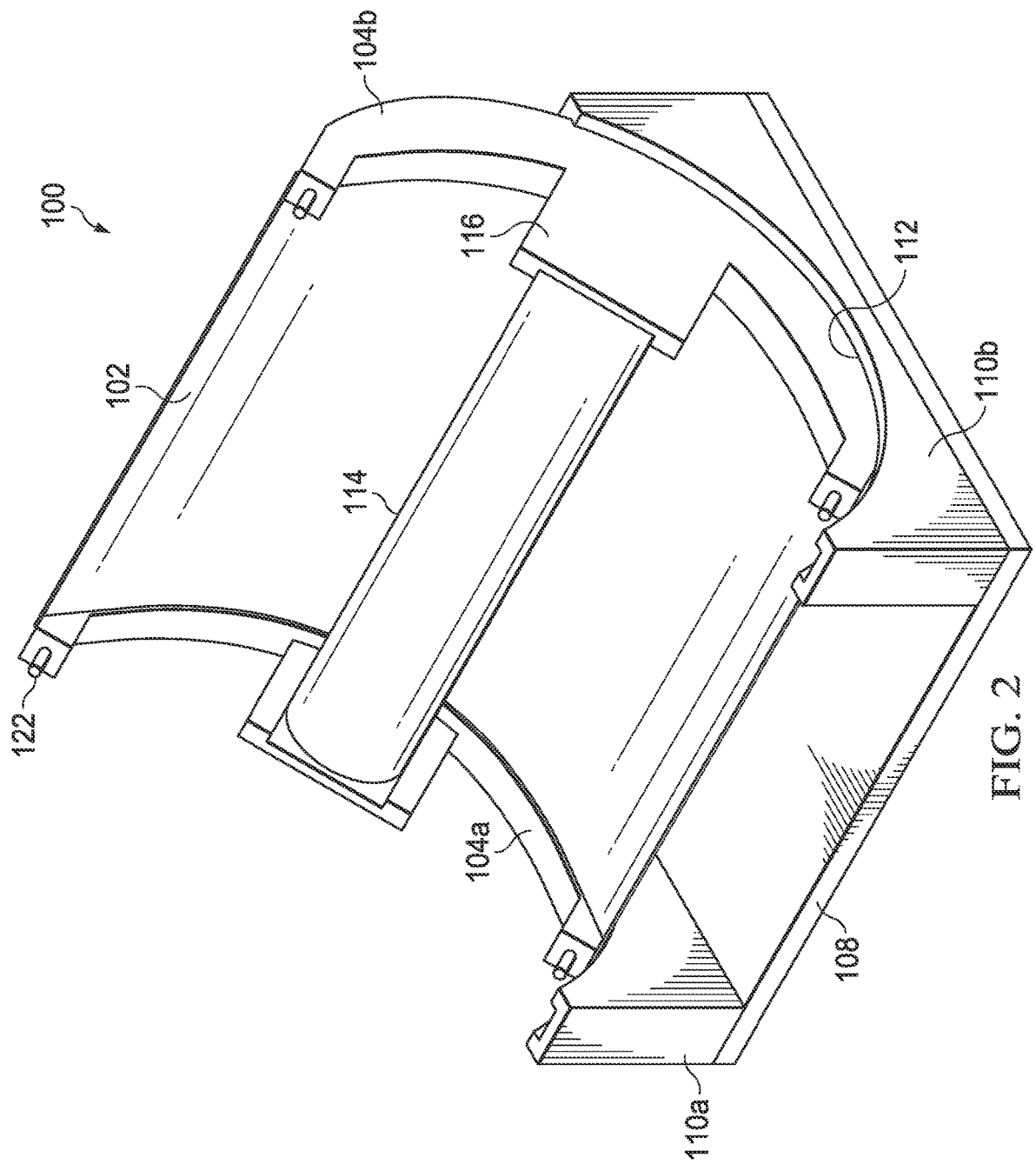
FIGS. 2 through 4 illustrate example views of the ultra-compact portable solar-powered thermo-chemical decontamination system of FIG. 1 in accordance with this disclosure.
Figure 3:
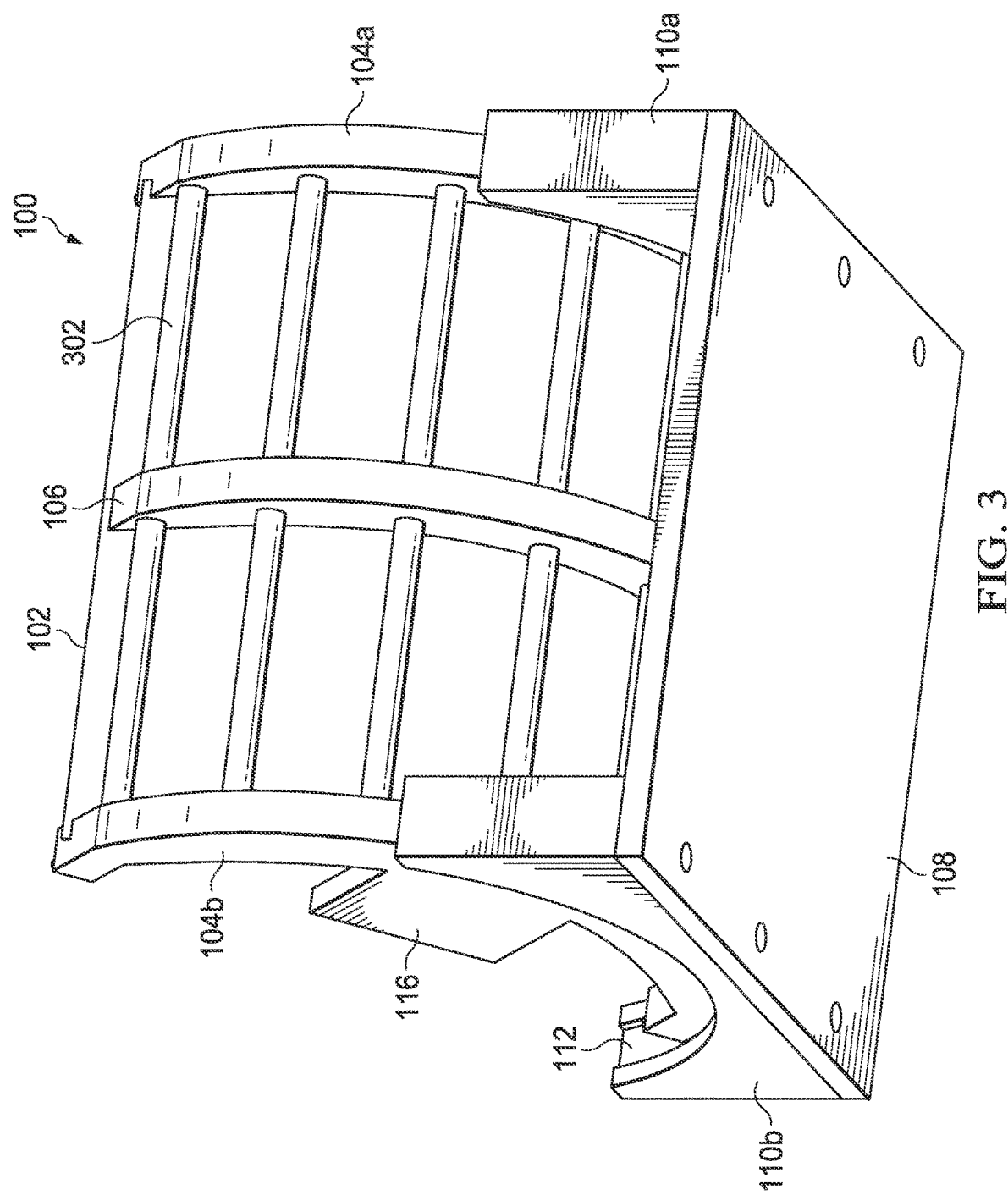
Figure 4:
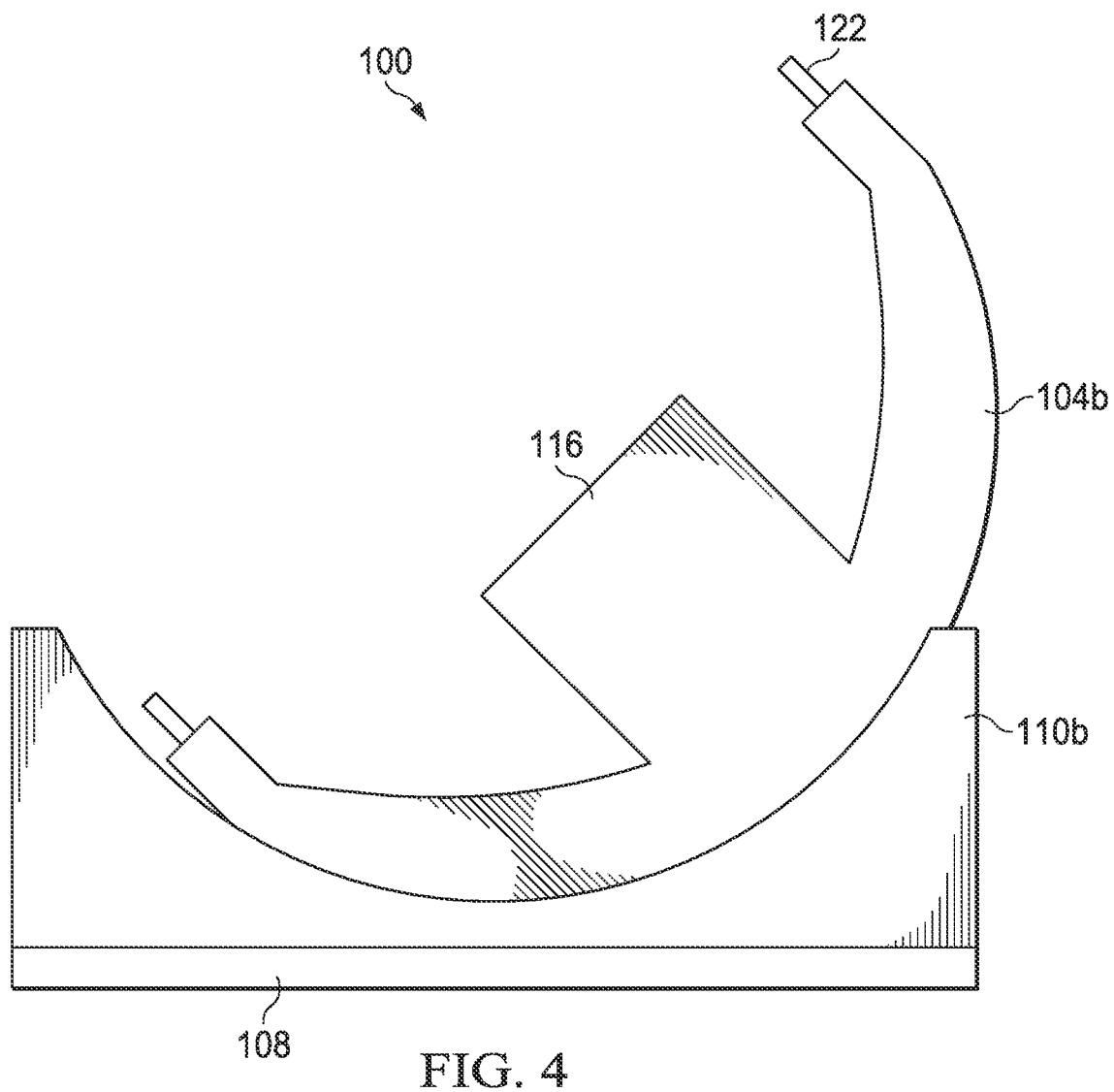

FIGS. 2 through 4 illustrate example views of the ultra-compact portable solar-powered thermo-chemical decontamination system 100 of FIG. 1 in accordance with this disclosure. More specifically, FIG. 2 illustrates a top perspective view of part of the decontamination system 100, FIG. 3 illustrates a bottom perspective view of part of the decontamination system 100, and FIG. 4 illustrates a side view of part of the decontamination system 100. Some components from FIG. 1 (such as the solar shade 118 and the telescope 124) have been removed from the decontamination system 100 shown in FIGS. 2 through 4 for ease of illustration and explanation.

As shown in FIG. 2, the containment vessel 114 can be positioned within the curvature of the solar reflector 102 in some embodiments. As noted above, the positioning of the containment vessel 114 can be based on the focal line of the solar reflector 102, which in this example is within the curvature of the solar reflector 102. Note, however, that the desired location of the containment vessel 114 can vary based on several factors, including the design of the solar reflector 102 (and therefore the location of the solar reflector's focal line).

As shown in FIG. 3, multiple support bars 302 can extend across the back side of the solar reflector 102. The support bars 302 can be used to couple the end supports 104a-104b and optionally the additional support(s) 106 together. For example, the support bars 302 can couple the end supports 104a-104b and any additional supports 106 so that these components rotate about a horizontal axis together as a unified structure. The ability to separate the end supports 104a-104b and any additional supports 106 also helps to facilitate compact storage of the decontamination system 100. Each support bar 302 may be formed from any suitable material(s), such as light-weight rugged plastic. Each support bar 302 may also be formed in any suitable manner, such as additive manufacturing, injection molding, casting, machining, or other suitable technique. Note that the number of support bars 302 and the positions of the support bars 302 here can vary as needed or desired. Also note that while support bars 302 extending continuously between the end supports 104a-104b are shown here, shorter support bars 302 may couple the end support 104a to an additional support 106, couple the end support 104b to an additional support 106, and (if present) couple multiple additional supports 106 to each other.

As shown in FIG. 4, the projections 122 of the end supports 104a-104b are positioned to extend in front of the projections 116. This allows the one or more solar shades 118 to be positioned in front of both the solar reflector 102 and the containment vessel 114 relative to the sun. Again, however, note that one or more solar shades 118 may be mounted on or otherwise attached to the decontamination system 100 in any other suitable manner. Also, it can be seen here that the end supports 104a-104b can rotate while maintaining contact with the side supports 110a-110b, which allows for elevation control of the solar reflector 102.

Figure 5:
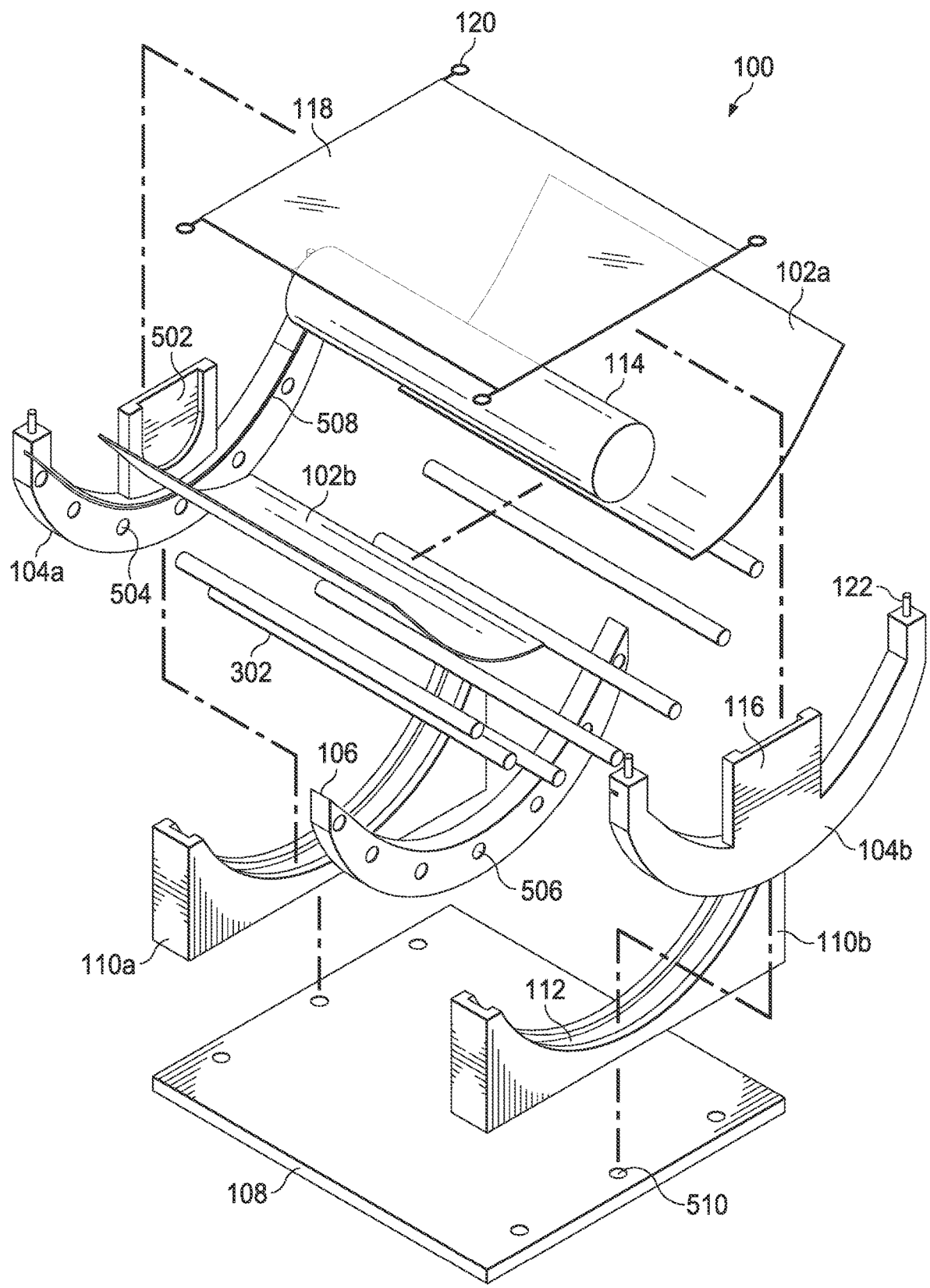
FIGS. 5 and 6 illustrate example exploded views of the ultra-compact portable solar-powered thermo-chemical decontamination system of FIG. 1 in accordance with this disclosure.
Figure 6:
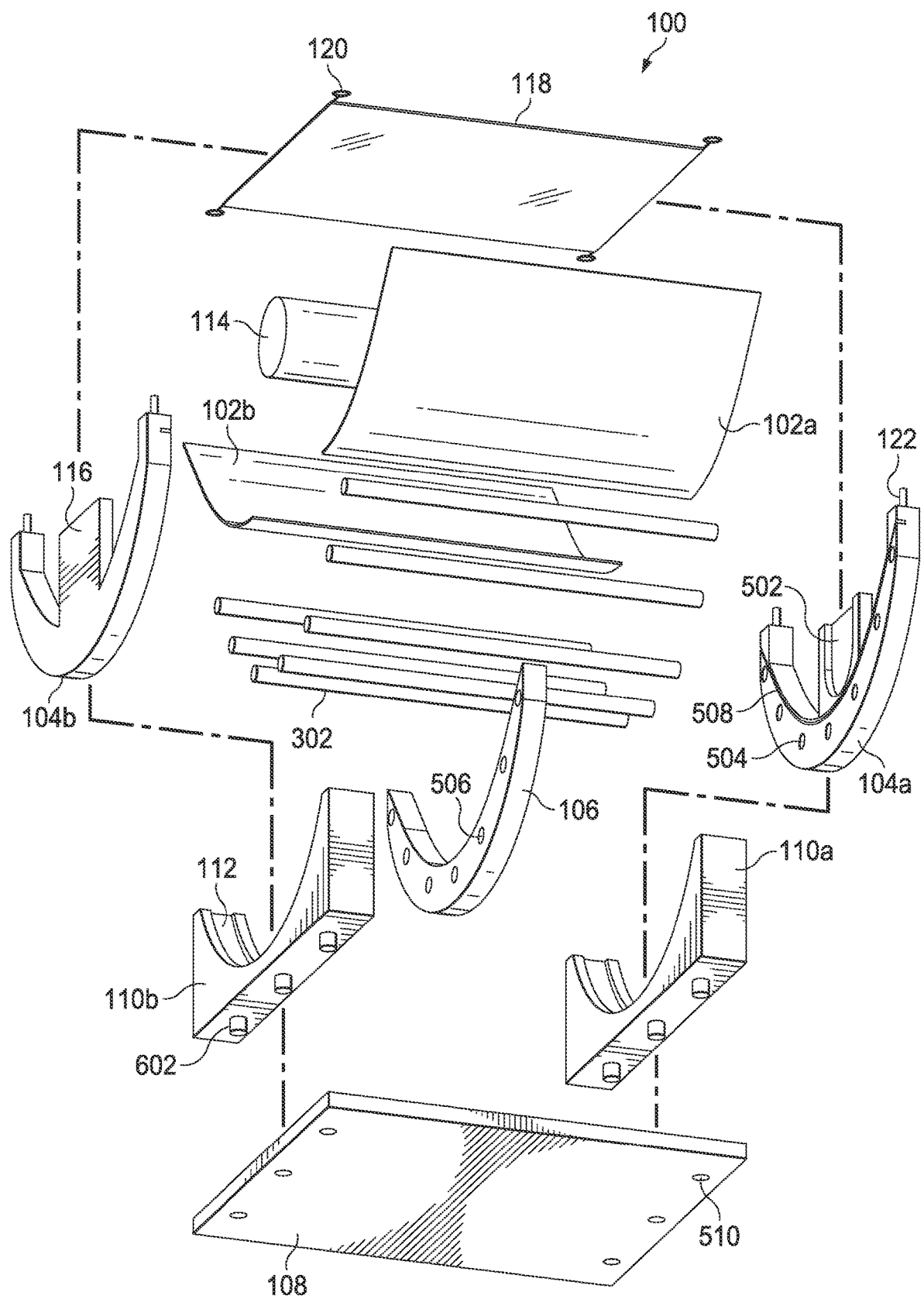

FIGS. 5 and 6 illustrate example exploded views of the ultra-compact portable solar-powered thermo-chemical decontamination system 100 of FIG. 1 in accordance with this disclosure. More specifically, FIG. 5 illustrates a top exploded view of the decontamination system 100, and FIG. 6 illustrates a bottom exploded view of the decontamination system 100.

As can be seen in FIGS. 5 and 6, each projection 116 includes a large groove or recess 502 that can be used to receive an end portion of the containment vessel 114. By positioning the end supports 104a-104b with a suitable spacing between the end supports 104a-104b, the containment vessel 114 can slide into and out of the grooves or recesses 502 of the projections 116 but otherwise be held in place by the projections 116. Moreover, the containment vessel 114 can be held in relatively the same location as the end supports 104a-104b are rotated. The grooves 112 in the side supports 110a-110b can be wide enough to accommodate the lower edges of the end supports 104a-104b. However, the grooves 112 can prevent the end supports 104a-104b from easily sliding off the side supports 110a-110b, which also helps to maintain the solar reflector 102 at a desired pointing direction.

Further, the end supports 104a-104b include openings 504 (which may or may not extend completely through the end supports 104a-104b), and each additional support 106 includes openings 506. The openings 504 and 506 receive portions of the support bars 302 in order to attach the end supports 104a-104b and the additional support(s) 106 together using the support bars 302. Moreover, each end support 104a-104b includes a groove 508, which is used to receive an edge portion of the solar reflector 102 in order to hold the solar reflector 102 in place and optionally maintain the shape of the solar reflector 102. As noted above, the solar reflector 102 may optionally be formed using multiple structures, which in FIGS. 5 and 6 include a first reflector 102a and a second reflector 102b. Here, the two edges of each reflector 102a-102b may be inserted into the grooves 508 of the end supports 104a-104b in order to hold the reflectors 102a-102b in place (and ideally up against or close to each other) to form the solar reflector 102.

In addition, the base 108 in this example includes openings 510 (which may or may not extend completely through the base 108), and each of the side supports 110a-110b includes multiple projections 602. The projections 602 are sized and shaped to be inserted into and retained within the openings 510 of the base 108, which helps to hold the side supports 110a-110b on the base 108. Note, however, that the base 108 and side supports 110a-110b may be connected to each other in any other suitable manner or formed as an integral structure.

As can be seen in the exploded views, the decontamination system 100 can be broken down into a number of smaller parts and stacked or otherwise arranged into a compact package for storage or transport. Moreover, the decontamination system 100 can be easily assembled and disassembled as needed, which allows for easy setup and breakdown of the decontamination system 100 at one or more desired locations.

Overall, the decontamination system 100 may have any suitable size, shape, and dimensions, and each component of the decontamination system 100 may have any suitable size, shape, and dimensions. As a particular example, the decontamination system 100 when broken down may be able to fit within a backpack that can be worn and transported by a user. Note, however, that other implementations of the decontamination system 100 are also possible with larger or smaller dimensions in assembled or stowed configurations.

In some embodiments, a decontamination process involving the decontamination system 100 may occur as follows. A suitable amount of liquid, such as low-concentration (like 3% to 6%) hydrogen peroxide solution, can be placed within the containment vessel 114. Also, a suitable amount of personal protection equipment or other equipment can be placed within the containment vessel 114 (possibly on a stand or other structure that separates the equipment from the outer wall of the containment vessel 114). The personal protection equipment or other equipment may or may not have been previously soaked in liquid, such as a low-concentration hydrogen peroxide solution. A lid of the containment vessel 114 can be secured to a remaining portion of the containment vessel 114, and the containment vessel 114 can be inserted between the projections 116 to a desired location. The solar reflector 102 can be aimed (possibly directly at the sun), and solar energy is reflected from the solar reflector 102 and heats the containment vessel 114. Among other things, this heats the personal protection equipment or other equipment within the containment vessel 114 and vaporizes at least a portion of the low-concentration hydrogen peroxide solution within the containment vessel 114. After the containment vessel 114 reaches a desired temperature threshold, the heating may continue for a specified time period, such as between about five minutes to about ten minutes. The heating can heat the personal protection equipment or other equipment to a temperature within a relatively-low temperature range, such as about 65° C. to about 80° C., to prevent damage to the equipment. The combination of heat and hydrogen peroxide can (given adequate temperature and time) decontaminate the personal protection equipment or other equipment within the containment vessel 114.

Once this part of the process is completed, the personal protection equipment or other equipment can be dried, which may occur in any suitable manner. For instance, in some cases, the personal protection equipment or other equipment may be removed from the containment vessel 114 and allowed to air dry (such as on a rack), or the personal protection equipment or other equipment may be removed from the containment vessel 114 and mechanically dried using a hair dryer or other heat or air source (assuming an adequately-reliable or accessible power source is available). In other cases, the lid of the containment vessel 114 may be removed, and the containment vessel 114 can again be heated (possibly in the same or similar manner as the first heating) so that moisture within the containment vessel 114 can escape and allow drying of the personal protection equipment or other equipment. Any other suitable approach for drying the personal protection equipment or other equipment may also be used here.

Although FIGS. 1 through 6 illustrate one example of an ultra-compact portable solar-powered thermo-chemical decontamination system 100, various changes may be made to FIGS. 1 through 6. For example, the sizes, shapes, and dimensions of the decontamination system 100 and its individual components can vary as needed or desired. Also, various components may be combined, further subdivided, replicated, omitted, or rearranged and additional components may be added according to particular needs. In addition, the decontamination system 100 may be used in any other suitable decontamination process and is not limited to the specific processes described above.

Figure 7A:
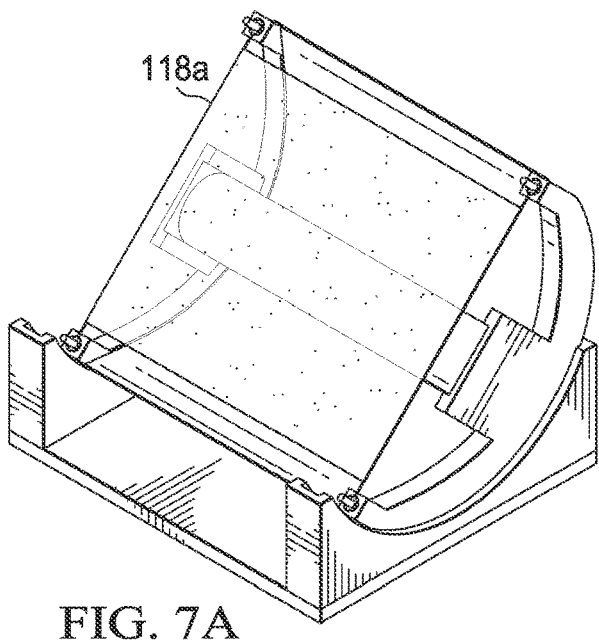
FIGS. 7A through 7C illustrate an example mechanism for controlling solar heating in the ultra-compact portable solar-powered thermo-chemical decontamination system of FIG. 1 in accordance with this disclosure.
Figure 7B:
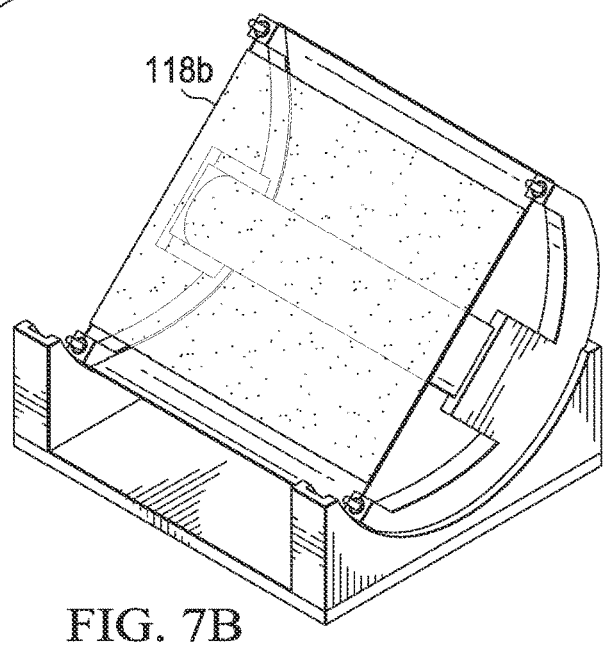
Figure 7C:
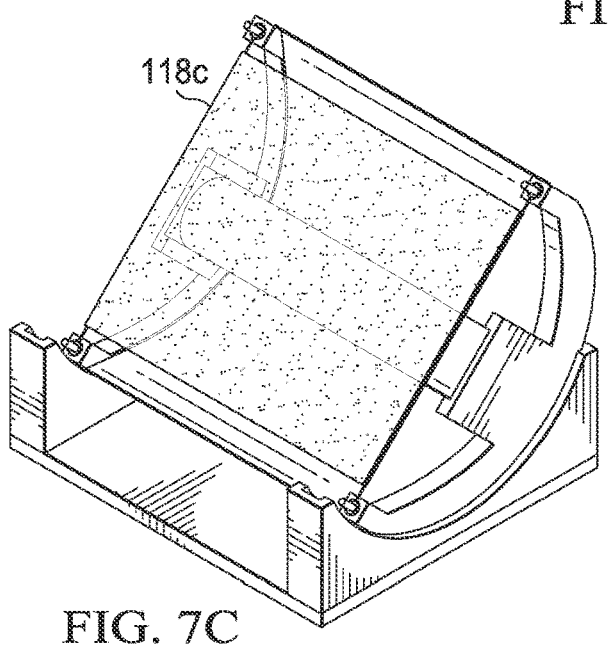

FIGS. 7A through 7C illustrate an example mechanism for controlling solar heating in the ultra-compact portable solar-powered thermo-chemical decontamination system 100 of FIG. 1 in accordance with this disclosure. As noted above, the number and/or semi-transparency of one or more solar shades 118 may be selected to provide a desired amount of solar flux control. In FIG. 7A, one or more solar shades 118a provide a first amount of solar flux control. This may, for example, involve mounting a single solar shade 118a on the end supports 104a-104b, where the single solar shade 118a provides a desired (relatively low) amount of solar flux control. In FIG. 7B, one or more solar shades 118b provide a second amount of solar flux control. This may, for example, involve mounting one or more solar shades 118b on the end supports 104a-104b, where the solar shade(s) 118b individually or collectively provide a larger amount of solar flux control (relative to FIG. 7A). In FIG. 7C, one or more solar shades 118c provide a third amount of solar flux control. This may, for example, involve mounting one or more solar shades 118c on the end supports 104a-104b, where the solar shade(s) 118c individually or collectively provide an even larger amount of solar flux control (relative to FIG. 7B). In this example, the use of no solar shades would provide the most solar energy to the solar reflector 102, while the use of the solar shades 118a-118c would respective provide smaller and smaller amounts of solar energy to the solar reflector 102.

As can be seen here, the one or more solar shades 118, 118a-118c provide the ability to easily control the solar flux reaching the solar reflector 102. This feature allows a user to limit the solar energy reaching the containment vessel 114 as needed or desired. Note that for conventional solar "cookers," such solar shades are unnecessary or even undesirable since there is often a lack of adequate solar energy for cooking purposes. For decontamination purposes, however, the ability to prevent overheating of the equipment being decontaminated in the containment vessel 114 may help to avoid damage to the equipment as described above.

Although FIGS. 7A through 7C illustrate one example of a mechanism for controlling solar heating in the ultra-compact portable solar-powered thermo-chemical decontamination system 100 of FIG. 1, various changes may be made to FIGS. 7A through 7C. For example, the decontamination system 100 may use any other suitable mechanism to control solar flux. Also, any suitable number of solar shades 118 may be used to support any suitable number of discrete solar flux control levels.

Note that a wide variety of other or additional features may be used in the decontamination system 100 as needed or desired. For example, FIGS. 8 and 9 illustrate example features that may be used with the ultra-compact portable solar-powered thermo-chemical decontamination system 100 of FIG. 1 in accordance with this disclosure.

Figure 8:
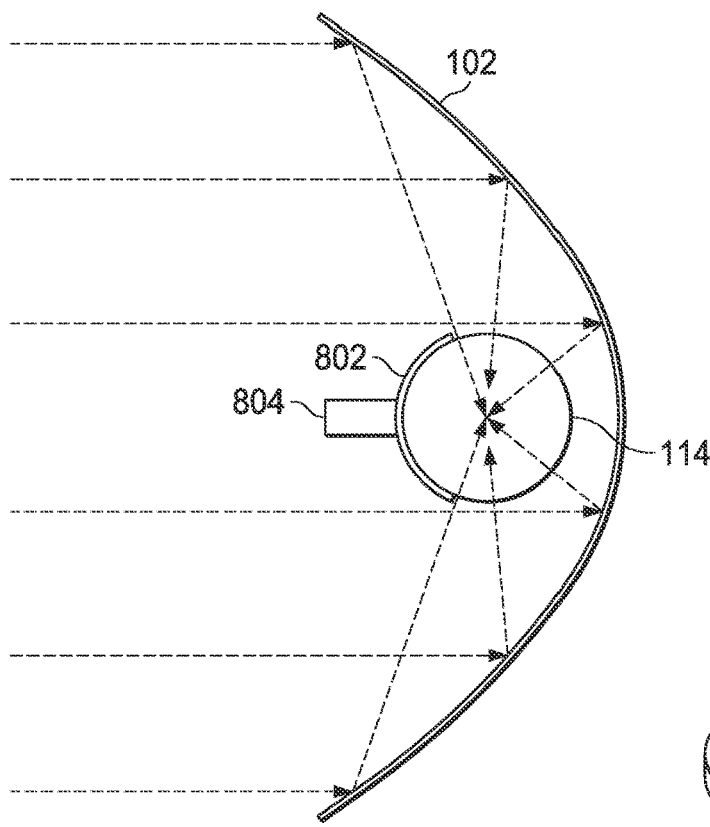
FIGS. 8 and 9 illustrate example features that may be used with the ultra-compact portable solar-powered thermo-chemical decontamination system of FIG. 1 in accordance with this disclosure.

As shown in FIG. 8, the "sun-facing" surface of the containment vessel 114 may receive much less solar energy than the surface of the containment vessel 114 facing the solar reflector 102. This is because the solar reflector 102 concentrates solar energy onto a portion of the exterior surface of the containment vessel 114. The sun-facing portion of the exterior surface of the containment vessel 114 receives less solar energy, and this portion of the containment vessel's surface may represent a potential heat leak. Thus, insulation 802 may be placed over that portion of the containment vessel's surface, where the insulation 802 helps to reduce heat loss through that portion of the containment vessel's surface. This can help to increase heating efficiency and reduce the time needed for a decontamination process to occur. Any suitable insulation 802 may be used here, and the insulation 802 may have any suitable form (such as single layer or multi-layer). The insulation 802 may be attached to the containment vessel 114 permanently or in a removable manner.

At least one handle 804 may also optionally be used with the containment vessel 114. The handle 804 can facilitate easier insertion and removal of the containment vessel 114 into and out of the decontamination system 100. Also, if the handle 804 is used in conjunction with the insulation 802, the handle 804 may be used to help ensure that the insulation 802 is positioned away from the solar reflector 102, such as by positioning the handle 804 so that the handle 804 faces away from the solar reflector 102. Note that the handle 804 may be coupled directly to the containment vessel 114 or indirectly, such as via the insulation 802. Also note that the handle 804 may be formed from one or more insulative materials, which may or may not be the same material(s) forming the insulation 802. In addition, note that the handle 804 may be used without using the insulation 802.

Figure 9:
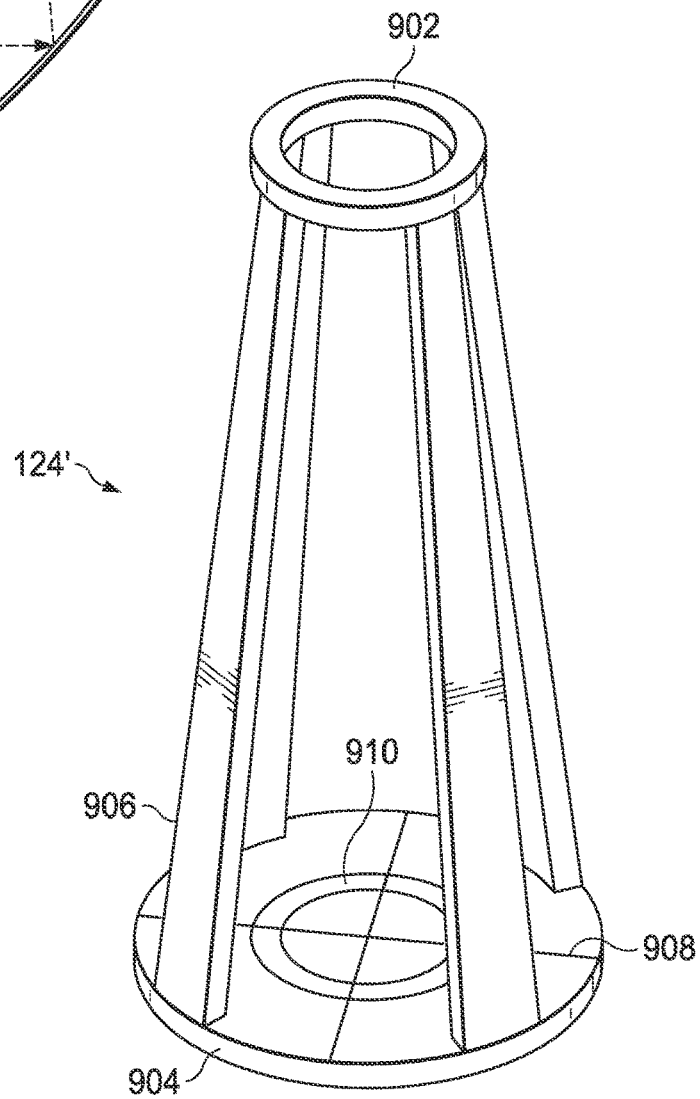

As shown in FIG. 9, an alternative optical sight 124' may be used in place of the telescope 124. Here, the optical sight 124' includes a ring 902 that is separated from a base 904 by various supports 906. The base 904 includes a crosshair or reticle 908, and the ring 902 can form a shadow 910 on the base 904 when the optical sight 124' is pointed at or near the sun. Centering the shadow 910 on the reticle 908 can help to point the optical sight 124' (and therefore the solar reflector 102) directly at the sun. Note that the two aiming mechanisms shown in FIGS. 1 and 9 are merely examples and that any other suitable mechanism can be used to aim the solar reflector 102 (or an aiming mechanism may be omitted in the decontamination system 100).

Other examples of features that may be used with the decontamination system 100 can include a temperature sensor within or on the containment vessel 114, where a user can view temperature readings to determine whether to add or remove a solar shade 118 or to continue or discontinue heating. A temperature sensor within or on the containment vessel 114 may also be used in conjunction with an electronic timer to trigger a countdown after a temperature threshold has been met (to ensure adequate heating of equipment being decontaminated), or the temperature sensor may be used in conjunction with an alert to trigger a warning when an excessive temperature is detected (to reduce or prevent damage to equipment being decontaminated). The base 108 of the decontamination system 100 may be placed on a rotatable mount or other mount that allows for azimuth control. One or more motorized drives may be used with an elevation mount and/or an azimuth mount to support motorized or electronic control of pointing and tracking of the solar reflector 102. The telescope 124 or other aiming mechanism may be configured to generate and output images to a control system, and the control system may use the images as part of a feedback look to control the motorized drive(s) in order to keep the solar reflector 102 pointed at the sun.

Although FIGS. 8 and 9 illustrate examples of features that may be used with the ultra-compact portable solar-powered thermo-chemical decontamination system 100 of FIG. 1, various changes may be made to FIGS. 8 and 9. For example, these features are for illustration only, and none, one, some, or all of these features may be implemented in any given decontamination system 100. Also note that any number of simpler or more advanced features can be added to the decontamination system 100 as needed or desired.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. An apparatus comprising:
a solar reflector configured to reflect solar energy towards a containment vessel;
end supports configured to receive and retain the solar reflector and the containment vessel and including shade connections;
a base comprising or coupled to multiple side supports, each side support configured to contact and support a corresponding one of the end supports; and
one or more semi-transparent solar shades removably mounted to the shade connections of the end supports and configured to reduce the solar energy reaching the solar reflector and the containment vessel.

2. The apparatus of claim 1, wherein:
the solar reflector comprises one or more reflectors; and
the end supports comprise grooves configured to receive edges of the one or more reflectors in order to hold the one or more reflectors in place and form the solar reflector.

3. The apparatus of claim 2, wherein the one or more reflectors are flexible and are configured to (i) bend when the edges of the one or more reflectors are inserted into the grooves of the end supports and (ii) revert to a substantially planar shape.

4. The apparatus of claim 1, wherein the end supports comprise projections configured to receive and hold the containment vessel such that a focal line of the solar reflector substantially coincides with a central longitudinal axis of the containment vessel.

5. The apparatus of claim 1, wherein each side support comprises a groove in which an edge of a corresponding one of the end supports is configured to slide in order to rotate the solar reflector.

6. The apparatus of claim 1, wherein the apparatus is configured to be disassembled for storage or transport and reassembled.

7. The apparatus of claim 1, wherein:
the one or more semi-transparent solar shades comprise multiple semi-transparent solar shades; and different solar shades or different combinations of solar shades have different levels of semi-transparency and are configured to reduce the solar energy reaching the solar reflector and the containment vessel by different amounts.

8. A system comprising:
a containment vessel configured to receive and retain equipment to be decontaminated;
a solar reflector configured to reflect solar energy towards the containment vessel in order to heat the containment vessel;
end supports configured to receive and retain the solar reflector and the containment vessel and including shade connections;
a base comprising or coupled to multiple side supports, each side support configured to contact and support a corresponding one of the end supports; and
one or more semi-transparent solar shades removably mounted to the shade connections of the end supports and configured to reduce the solar energy reaching the solar reflector and the containment vessel.

9. The system of claim 8, wherein:
the solar reflector comprises one or more reflectors; and
the end supports comprise grooves configured to receive edges of the one or more reflectors in order to hold the one or more reflectors in place and form the solar reflector.

10. The system of claim 9, wherein the one or more reflectors are flexible and are configured to (i) bend when the edges of the one or more reflectors are inserted into the grooves of the end supports and (ii) revert to a substantially planar shape.

11. The system of claim 8, wherein the end supports comprise projections configured to receive and hold the containment vessel such that a focal line of the solar reflector substantially coincides with a central longitudinal axis of the containment vessel.

12. The system of claim 8, wherein each side support comprises a groove in which an edge of a corresponding one of the end supports is configured to slide in order to rotate the solar reflector.

13. The system of claim 8, wherein:
the one or more semi-transparent solar shades comprise multiple semi-transparent solar shades; and
different solar shades or different combinations of solar shades have different levels of semi-transparency and are configured to reduce the solar energy reaching the solar reflector and the containment vessel by different amounts.

14. The system of claim 8, wherein:
the containment vessel comprises a cylindrical containment vessel; and
the solar reflector comprises a parabolic cylindrical reflector.

15. The system of claim 8, further comprising:
a telescope or optical sight configured to facilitate aiming of the solar reflector.

16. The system of claim 8, further comprising:
an insulation covering a portion of the containment vessel;
wherein the containment vessel is configured to be inserted between the end supports with the insulation facing away from the solar reflector.

17. The system of claim 8, wherein the containment vessel comprises a handle, the containment vessel configured to be inserted between the end supports with the handle facing away from the solar reflector.

18. A method comprising:
inserting a containment vessel containing equipment to be decontaminated between end supports of a decontamination system;
reflecting solar energy towards the containment vessel using a solar reflector of the decontamination system, wherein edges of the solar reflector are received and retained by the end supports;
using a base comprising or coupled to multiple side supports, supporting the end supports and allowing the end supports to rotate in order to aim the solar reflector; and
using one or more semi-transparent solar shades removably mounted to shade connections on the end supports to control the solar energy reaching the solar reflector.

19. The method of claim 18, further comprising:
changing an amount of the solar energy reaching the solar reflector by (i) altering a number of solar shades being used or (ii) altering the one or more solar shades being used.

20. The method of claim 18, further comprising:
inserting a low-concentration hydrogen peroxide solution into the containment vessel with the equipment to be decontaminated; and
heating the low-concentration hydrogen peroxide solution and the equipment to be decontaminated in the containment vessel using the solar energy.

* * * * *